United States Patent
Tomari et al.

(10) Patent No.: US 11,905,374 B2
(45) Date of Patent: Feb. 20, 2024

(54) CONDUCTIVE MEMBER, BIOELECTRODE, AND BIOSIGNAL MEASURING DEVICE

(71) Applicant: FUJIFILM Business Innovation Corp., Tokyo (JP)

(72) Inventors: Shogo Tomari, Kanagawa (JP); Wataru Yamada, Kanagawa (JP); Monta Ido, Kanagawa (JP); Tadashi Suto, Kanagawa (JP)

(73) Assignee: FUJIFILM Business Innovation Corp., Tokyo (JP)

( * ) Notice: Subject to any disclaimer, the term of this patent is extended or adjusted under 35 U.S.C. 154(b) by 990 days.

(21) Appl. No.: 16/740,473

(22) Filed: Jan. 12, 2020

(65) Prior Publication Data

US 2021/0070943 A1    Mar. 11, 2021

(30) Foreign Application Priority Data

Sep. 6, 2019  (JP) .................................. 2019-162702

(51) Int. Cl.
| | | |
|---|---|---|
| *C08G 77/04* | (2006.01) | |
| *C08K 3/04* | (2006.01) | |
| *A61B 5/25* | (2021.01) | |

(52) U.S. Cl.
CPC .............. *C08G 77/045* (2013.01); *A61B 5/25* (2021.01); *C08K 3/04* (2013.01); *C08K 2201/001* (2013.01)

(58) Field of Classification Search
None
See application file for complete search history.

(56) References Cited

U.S. PATENT DOCUMENTS

2017/0251941 A1    9/2017  Hatakeyama et al.
2019/0359872 A1*  11/2019  Yoo .......................... C09K 5/00

FOREIGN PATENT DOCUMENTS

| JP | S6247374 | | 3/1987 |
|---|---|---|---|
| JP | H02206546 | | 8/1990 |
| JP | H02242855 | | 9/1990 |
| JP | 2007086394 | | 4/2007 |
| JP | 2008074913 | | 4/2008 |
| JP | 2008163282 | | 7/2008 |
| JP | 2011219687 | | 11/2011 |
| JP | 2013045012 A | * | 3/2013 |
| JP | 2018011931 | | 1/2018 |
| JP | 2018033769 | | 3/2018 |
| KR | 20180093817 A | * | 8/2018 |
| WO | 2018230445 | | 12/2018 |

OTHER PUBLICATIONS

Nagaoka et al., JP-2013045012-A, Mar. 4, 2013 (Machine translation) (Year: 2013).*
Hatakeyama et al., KR20180093817A, Aug. 22, 2018 (Machine translation) (Year: 2018).*
"Office Action of Japan Counterpart Application", dated May 9, 2023, with English translation thereof, p. 1-p. 9.
"Decision of Refusal of Japan Counterpart Application", dated Sep. 26, 2023, with English translation thereof, p. 1-p. 11.

* cited by examiner

*Primary Examiner* — Cheng Yuan Huang
(74) *Attorney, Agent, or Firm* — JCIPRNET (57) ABSTRACT

A conductive member contains silicone rubber and a conductive agent. The total content of cyclic dimethylpolysiloxane having 3 to 24 silicon atoms in the conductive member is 5000 ppm or less.

12 Claims, 2 Drawing Sheets

CONDUCTIVE MEMBER, BIOELECTRODE, AND BIOSIGNAL MEASURING DEVICE

CROSS-REFERENCE TO RELATED APPLICATIONS

This application is based on and claims priority under 35 USC 119 from Japanese Patent Application No. 2019-162702 filed Sep. 6, 2019.

BACKGROUND

(i) Technical Field

The present disclosure relates to a conductive member, a bioelectrode, and a biosignal measuring device.

(ii) Related Art

Japanese Unexamined Patent Application Publication No. 2018-11931 discloses a bioelectrode having a resin layer containing dispersed particles, the surface of the particles being covered with gold, silver, or platinum.

Japanese Unexamined Patent Application Publication No. 2018-33769 discloses a bioelectrode containing AS resin, ABS resin, and carbon fiber.

SUMMARY

Aspects of non-limiting embodiments of the present disclosure relate to a conductive member having a lower volume resistivity compared with a conductive member containing silicone rubber and a conductive agent wherein the total content of cyclic dimethylpolysiloxane having 3 to 24 silicon atoms is more than 5000 ppm.

Aspects of certain non-limiting embodiments of the present disclosure address the above advantages and/or other advantages not described above. However, aspects of the non-limiting embodiments are not required to address the advantages described above, and aspects of the non-limiting embodiments of the present disclosure may not address advantages described above.

According to an aspect of the present disclosure, there is provided a conductive member containing silicone rubber and a conductive agent, wherein a total content of cyclic dimethylpolysiloxane having 3 to 24 silicon atoms is 5000 ppm or less.

BRIEF DESCRIPTION OF THE DRAWINGS

An exemplary embodiment of the present disclosure will be described in detail based on the following figures, wherein.

DETAILED DESCRIPTION

Hereafter, an exemplary embodiment of the present disclosure will be described. The description and examples merely exemplify the exemplary embodiment and do not limit the scope of the exemplary embodiment.

In the present disclosure, every numerical range expressed by using "to" refers to a range inclusive of the numerical values before and after "to" as the minimum and maximum values, respectively.

In numerical ranges presented in a staged manner in the present disclosure, the upper limit value or the lower limit value indicated in one numerical range may be replaced by the upper limit value or the lower limit value in other numerical ranges presented in a staged manner. Furthermore, in numerical ranges in the present disclosure, the upper limit value or the lower limit value may be replaced by a value described in Examples.

In the present disclosure, in the description of the exemplary embodiment with reference to the drawings, the configuration of the exemplary embodiment is not limited to the configuration illustrated in the drawings. Furthermore, the sizes of members in each of the drawings are conceptual and do not limit the relative relationships between the members in terms of size.

In the present disclosure, each component may contain two or more substances corresponding to each component. In the present disclosure, when there are two or more substances corresponding to each component present in a composition, the amount of each component contained in the composition refers to the total amount of the two or more substances present in the composition unless otherwise indicated.

In the present disclosure, two or more particles corresponding to each component may be contained in the composition. When two or more particles corresponding to each component are present in the composition, the particle size of each component refers to the value of a mixture of two or more particles present in the composition unless otherwise indicated.

Conductive Member

A conductive member according to the present exemplary embodiment contains silicone rubber and a conductive agent, and the total content (by mass) of cyclic dimethylpolysiloxane having 3 to 24 silicon atoms is 5000 ppm or less. The term "ppm" is short for "parts per million".

Cyclic dimethylpolysiloxane having 3 to 24 silicon atoms is a chemical substance represented by Formula below. In Formula below, n is an integer of 3 to 24.

In the present disclosure, cyclic dimethylpolysiloxane having n number of silicon atoms is referred to as "Dn cyclic dimethylpolysiloxane" and cyclic dimethylpolysiloxane having 3 to 24 silicon atoms is referred to as "D3 to D24 cyclic dimethylpolysiloxane".

As a conductive member forming a biocontact portion of a bioelectrode, a conductive member in which a conductive agent (e.g., carbon black) is blended with silicone rubber is conventionally known. While excelling in biological safety, silicone rubber has insulation properties; thus, conductivity is imparted to silicone rubber by blending the conductive agent therein.

Research by the inventors has revealed that the volume resistivity of a finished product of the conductive member is higher than the design value of the volume resistivity. Additional research by the inventors has revealed that the volume resistivity may be lowered by decreasing the content of D3 to D24 cyclic dimethylpolysiloxane.

It is already known that a low-molecular-weight organopolysiloxane is volatilized in an electrical apparatus to form an insulating film of silicon dioxide on a surface of a member; however, the mechanism by which the present exemplary embodiment may provide a conductive member having a low volume resistivity is probably due to the decrease in the amount of D3 to D24 cyclic dimethylpolysiloxane contained in the conductive member and not due to the suppression of insulating film formation. This is because a test conducted in an open space immediately after the production of the conductive member (i.e., under conditions where insulation film formation on the surface of the conductive member hardly occurs) has indicated that the volume resistivity of the conductive member and the content of D3 to D24 cyclic dimethylpolysiloxane are correlated with each other.

When the total content of D3 to D24 cyclic dimethylpolysiloxane exceeds 5000 ppm in a conductive member containing silicone rubber and a conductive agent, the volume resistivity of the conductive member becomes excessively high, which hinders highly precise measurement of biosignals. In view of lowering the volume resistivity of the conductive member, the total content of D3 to D24 cyclic dimethylpolysiloxane in the conductive member is preferably 5000 ppm or less, more preferably 4000 ppm or less, and even more preferably 3000 ppm or less. In view of lowering the volume resistivity of the conductive member, the total content of D3 to D24 cyclic dimethylpolysiloxane in the conductive member is preferably as small as possible.

In view of lowering the volume resistivity of the conductive member, the total content of D3 to D24 cyclic dimethylpolysiloxane in the conductive member according to the present exemplary embodiment is preferably as small as possible, most preferably 0 ppm. However, depending on the procedure for removing D3 to D24 cyclic dimethylpolysiloxane from the conductive member (which will be described in detail later), the rubber hardness of the silicone rubber may be increased and the flexibility of the conductive member may be decreased. Thus, the procedure for removing D3 to D24 cyclic dimethylpolysiloxane is preferably performed gently, and accordingly, a certain amount of D3 to D24 cyclic dimethylpolysiloxane is acceptable. The lower limit of the content of D3 to D24 cyclic dimethylpolysiloxane in the conductive member according to the present exemplary embodiment is, for example, 0 ppm or more, more than 0 ppm, 1 ppm or more, 5 ppm or more, 10 ppm or more, 50 ppm or more, 100 ppm or more, or 500 ppm or more.

In the present exemplary embodiment, the total content (ppm) of D3 to D24 cyclic dimethylpolysiloxane is a value denoted by (total amount of D3 to D24 cyclic dimethylpolysiloxane contained in conductive member/total amount of conductive member) converted to parts per million by mass.

The total amount of D3 to D24 cyclic dimethylpolysiloxane contained in the conductive member is measured using a gas chromatograph mass spectrometer (GCMS-QP2020, manufactured by Shimadzu Corporation) and a nonpolar column (Rtx-1, 10157, film thickness: 1.00 µm, length: 60 m, inner diameter: 0.32 mm, manufactured by Restek Corporation) using a headspace method. The specific identification method is as follows.

The conductive member is immersed in a solvent that dissolves silicone rubber (e.g., 10 ml of acetone containing n-tetradecane (20 µg/ml)) to dissolve the silicone rubber, and a portion of the liquid component is put into a vial. The vial is sealed with a cap, and the temperature is raised to 190° C. for a heating time of 3 minutes. The volatilized component in the vial is introduced into the column, and the detection of D3 to D24 cyclic dimethylpolysiloxane is performed under the following conditions.

Carrier gas type: Helium
Carrier gas pressure: 120 kPa (constant pressure)
Oven temperature: 40° C. (5 minutes)→(15° C./min)→ 250° C. (6 minutes) (25 minutes in total)
Ion source temperature: 260° C.
Interface temperature: 260° C.

Standard solutions prepared by diluting a reference material (D4 cyclic dimethylpolysiloxane, i.e., octamethylcyclotetrasiloxane) with ethanol and having different concentrations are used to construct a calibration curve. The amount of each of D3, D4, . . . , D23, and D24 is determined from the peak area of each of D3, D4, . . . , D23, and D24 that appears in the chromatogram of the sample and the calibration curve of the reference material. The total amount of D3 to D24 is then determined. Furthermore, the total content (ppm) of D3 to D24 cyclic dimethylpolysiloxane with respect to the total amount of the conductive member is calculated.

In view of lowering the volume resistivity, the total content of cyclic dimethylpolysiloxane having 3 to 12 silicon atoms (referred to as "D3 to D12 cyclic dimethylpolysiloxane") in the conductive member according to the present exemplary embodiment is preferably 500 ppm or less, more preferably 400 ppm or less, and even more preferably 300 ppm or less.

The lower limit of the content of D3 to D12 cyclic dimethylpolysiloxane in the conductive member according to the present exemplary embodiment is, for example, 0 ppm or more, more than 0 ppm, 1 ppm or more, 5 ppm or more, 10 ppm or more, 50 ppm or more, or 100 ppm or more.

Examples of use of the conductive member according to the present exemplary embodiment include biocontact portions of bioelectrodes, ear pieces, nose pads for glasses, and internal headband portions of hats and caps.

Hereafter, the components, composition, and physical properties of the conductive member according to the present exemplary embodiment will be described in detail.

Silicone Rubber Examples of a rubber raw material for the silicone rubber include millable silicone rubber, liquid silicone rubber, room-temperature-curing silicone rubber, high-temperature-curing silicone rubber, condensation-reaction silicone rubber, addition-reaction silicone rubber, and ultraviolet-curing silicone rubber.

Examples of the rubber raw material for the silicone rubber also include methyl silicone rubber (MQ), vinyl methyl silicone rubber (VMQ), phenyl methyl silicone rubber (PMQ), phenyl vinyl methyl silicone rubber (PVMQ), and fluoro vinyl methyl silicone rubber (FVMQ).

Various additives may be added to the rubber raw material for the silicone rubber according to the type of curing reaction. Examples of the additives include vulcanizing agents, vulcanization accelerators, platinum catalysts for crosslinking, addition reaction control agents (e.g., a quencher for suppressing the effect of a platinum catalyst in a low-temperature environment), crosslinking agents, photoacid generators, and photoradical generators.

Conductive Agent

The conductive agent may be any of an electronic conductive agent, an ionic conductive agent, a conductive polymer, and the like. The conductive agent is preferably made of conductive particles, examples of which include carbon black; particles of metals such as gold, silver, and copper; particles of metal oxides such as titanium oxide, zinc oxide, and tin oxide; and particles of barium sulfate, aluminum borate, potassium titanate, and the like. Among them, carbon black is preferable in view of the compatibility with the silicone rubber.

In view of dispersibility in the silicone rubber, the average primary particle size of the conductive agent is preferably 10 nm or more and 100 nm or less, more preferably 20 nm or more and 80 nm or less, and even more preferably 25 nm or more and 50 nm or less.

The average primary particle size of the conductive agent is measured using the following method.

The conductive member is cut with a microtome to collect a sample having a thickness of 200 nm, and a cross section of the sample is observed under a transmission electron microscope (TEM). The long diameters of 50 primary particles of the conductive agent are measured, and the arithmetic average of the measured values is calculated to determine the average primary particle size.

The total content of the conductive agent is, for example, 40 parts by mass or more and 80 parts by mass or less with respect to 100 parts by mass of the silicone rubber.

Carbon Black

Examples of the carbon black include furnace black, thermal black, channel black, Ketjen black, acetylene black, and color black.

To achieve low resistance in the conductive member, a carbon black having a higher DBP absorption is more effective than a carbon black having a lower DBP absorption.

On the other hand, a carbon black having a higher DBP absorption has a higher reinforcement effect on a rubber material than a carbon black having a lower DBP absorption; thus, the conductive member tends to have a higher rubber hardness when a carbon black having a higher DBP absorption is blended therein. Thus, to improve the dynamic conformance of the conductive member, a carbon black having a lower DBP absorption is more effective than a carbon black having a higher DBP absorption. Furthermore, depending on the procedure for removing D3 to D24 cyclic dimethylpolysiloxane from the conductive member (which will be described in detail later), the silicone rubber may have a higher rubber hardness, and as a result, the conductive member may have lower flexibility. In view of this, the use of a carbon black having a lower DBP absorption is preferable.

Accordingly, in view of combining the low resistance and the dynamic conformance of the conductive member, the conductive member according to the present exemplary embodiment preferably contains both a carbon black having a relatively lower DBP absorption and a carbon black having a relatively higher DBP absorption. Specifically, the conductive member according to the present exemplary embodiment preferably contains a first carbon black having a DBP absorption of less than 200 $cm^3/100$ g (preferably not less than 50 $cm^3/100$ g and not more than 200 $cm^3/100$ g) and a second carbon black having a DBP absorption of not less than 200 $cm^3/100$ g (preferably not less than 200 $cm^3/100$ g and not more than 500 $cm^3/100$ g).

The DBP absorption of carbon black is the amount ($cm^3$) of dibutyl phthalate (DBP) absorbed per 100 g of carbon black and is a value defined by ASTM D2414-6TT.

In view of combining the low resistance and the dynamic conformance of the conductive member, the absolute value of the difference in the DBP absorption between the first carbon black and the second carbon black is preferably not less than 70 $cm^3/100$ g and not more than 400 $cm^3/100$ g, more preferably not less than 100 $cm^3/100$ g and not more than 350 $cm^3/100$ g, even more preferably not less than 120 $cm^3/100$ g and not more than 300 $cm^3/100$ g, and still even more preferably not less than 150 $cm^3/100$ g and not more than 250 $cm^3/100$ g.

When two or more first carbon blacks are used in combination, the DBP absorption of the first carbon blacks is equal to a weighted average calculated by weighting the DBP absorption of individual carbon blacks corresponding to the first carbon blacks by the content ratio (by mass) of the individual carbon blacks. When two or more second carbon blacks are used in combination, the DBP absorption of the second carbon blacks is equal to a weighted average calculated by weighting the DBP absorption of individual carbon blacks corresponding to the second carbon blacks by the content ratio (by mass) of the individual carbon blacks.

The DBP absorption of the total carbon blacks contained in the conductive member (referring to a weighted average calculated by weighting the DBP absorption of individual carbon blacks by the content ratio (by mass) of the individual carbon blacks) is preferably not less than 80 $cm^3/100$ g and not more than 450 $cm^3/100$ g, more preferably not less than 90 $cm^3/100$ g and not more than 400 $cm^3/100$ g, even more preferably not less than 100 $cm^3/100$ g and not more than 350 $cm^3/100$ g, and still even more preferably not less than 120 $cm^3/100$ g and not more than 300 $cm^3/100$ g.

Examples of the first carbon black include the following carbon blacks.

Asahi Thermal, manufactured by Asahi Carbon Co., Ltd., DBP absorption: 28 $cm^3/100$ g Asahi #50U, manufactured by Asahi Carbon Co., Ltd., DBP absorption: 63 $cm^3/100$ g Asahi #70L, manufactured by Asahi Carbon Co., Ltd., DBP absorption: 75 $cm^3/100$ g

3030B, manufactured by Mitsubishi Chemical Corporation, DBP absorption: 130 $cm^3/100$ g

3050B, manufactured by Mitsubishi Chemical Corporation, DBP absorption: 175 $cm^3/100$ g Examples of the second carbon black include the following carbon blacks.

Asahi F-200SHS, manufactured by Asahi Carbon Co., Ltd., DBP absorption: 220 $cm^3/100$ g FX35, manufactured by Denka Co., Ltd., DBP absorption: 220 $cm^3/100$ g ECP200L, manufactured by Lion Specialty Chemicals Co., Ltd., DBP absorption: 300 $cm^3/100$ g EC300J, manufactured by Lion Specialty Chemicals Co., Ltd., DBP absorption: 365 $cm^3/100$ g LIONITE CB, manufactured by Lion Specialty Chemicals Co., Ltd., DBP absorption: 378 $cm^3/100$ g ECP600JD, manufactured by Lion Specialty Chemicals Co., Ltd., DBP absorption: 495 $cm^3/100$ g HS 500, manufactured by Asahi Carbon Co., Ltd., DBP absorption: 500 $cm^3/100$ g The carbon black is preferably an oxidized carbon black on the surface of which an oxygen-containing functional group (e.g., a carboxy group, a quinone group, a lactone group, or a hydroxy group) is formed through an oxidation process. An oxidized carbon black is obtainable by, for example, an air oxidation method in which carbon black is exposed to and reacted with air in a high-temperature environment, an oxidation method in which carbon black is reacted with nitrogen oxide, ozone, or the like at normal temperature, or another oxidation method in which carbon black is subjected to air oxidation at high temperature followed by ozone oxidation at low temperature.

The pH of the carbon black is preferably 2 or more and 10 or less, more preferably 5 or more and 9 or less. The pH of the carbon black is measured using a pH measurement method prescribed by JIS Z8802:2011 and is equal to the pH of a dispersion liquid prepared by adding 50 g of carbon black to 1000 ml of water at 20° C. and stirring the mixture.

In view of dispersibility in the silicone rubber, the average primary particle size of the carbon black is preferably 10 nm or more and 100 nm or less, more preferably 20 nm or more and 80 nm or less, and even more preferably 25 nm or more and 50 nm or less.

The average primary particle size of the carbon black is measured using the following method.

The conductive member is cut with a microtome to collect a sample having a thickness of 200 nm, and a cross section of the sample is observed under a transmission electron microscope (TEM). The long diameters of 50 primary particles of the carbon black are measured, and the arithmetic average of the measured values is calculated to determine the average primary particle size.

In view of combining the low resistance and the dynamic conformance of the conductive member, the total content of the carbon black is preferably 40 parts by mass or more and 80 parts by mass or less, more preferably 50 parts by mass or more and 70 parts by mass or less with respect to 100 parts by mass of the silicone rubber.

In view of combining the low resistance and the dynamic conformance of the conductive member, the total content of the second carbon black is preferably 10 parts by mass or more and 30 parts by mass or less, more preferably 15 parts by mass or more and 25 parts by mass or less with respect to 100 parts by mass of the silicone rubber.

The total content of the second carbon black is, for example, 10% by mass or more and 80% by mass or less, 15% by mass or more and 75% by mass or less, 20% by mass or more and 70% by mass or less, or 25% by mass or more and 65% by mass or less with respect to the total amount of the first carbon black and the second carbon black.

Other Additives

Examples of other additives include foaming agents, flame retardants, antioxidants, ultraviolet absorbers, foam stabilizers, fillers (e.g., silica, calcium carbonate), coupling agents (added, for example, to improve the dispersibility of the carbon black), and coloring agents.

Method of Manufacturing Conductive Member

The conductive member according to the present exemplary embodiment may be manufactured by any method. The conductive member according to the present exemplary embodiment is manufactured, for example, by putting a rubber compound containing a silicone rubber raw material, a conductive agent, and other additives into a mold and heating the rubber compound.

The D3 to D24 cyclic dimethylpolysiloxane contained in the silicone rubber may be removed by heating and volatilizing the silicone rubber. Thus, the method of manufacturing the conductive member according to the present exemplary embodiment preferably includes a vulcanizing process to cure a silicone rubber raw material and a heating process to remove D3 to D24 cyclic dimethylpolysiloxane from the silicone rubber that has been cured.

The vulcanizing process is, for example, a process of heating the rubber compound put into the mold. The heating temperature and the heating time in the vulcanizing process are selected according to the type of curing reaction of the silicone rubber raw material and the composition of the silicone rubber raw material.

In the heating process to remove D3 to D24 cyclic dimethylpolysiloxane from the silicone rubber that has been cured, the heating conditions are desirably set according to the thickness of the silicone rubber. To remove D3 to D24 cyclic dimethylpolysiloxane, as the thickness of the silicone rubber increases, the heating temperature or the heating time is desirably increased. On the other hand, because the silicone rubber tends to be harder as the heating temperature or the heating time increases, the heating conditions are desirably set so as not to impair the dynamic conformance of the silicone rubber. Examples of the heating temperature include 100° C. to 300° C. and 150° C. to 250° C. The heating time may be constant or varied. Examples of the heating time include 1 to 14 hours and 3 to 12 hours.

To facilitate the volatilization of D3 to D24 cyclic dimethylpolysiloxane, the heating process may be performed under reduced pressure. To suppress the adhesion of the D3 to D24 cyclic dimethylpolysiloxane that has been volatilized to the surface of the conductive member, performing a heating process while drawing gas in a heating furnace with a vacuum pump is also desirable.

On the surface of the conductive member subjected to the heating process, a blasting process, such as shotblasting, sandblasting, or liquid blasting may be performed.

Physical Property Values of Conductive Member

The conductive member according to the present exemplary embodiment is suitable for use in a biocontact portion of a bioelectrode for measuring weak potentials inside a living body with an electrode placed on the surface of the living body. The desirable physical property values of the conductive member according to the present exemplary embodiment when applied to a biocontact portion of a bioelectrode are as follows.

In view of low resistance, the volume resistivity of the conductive member is preferably $1 \times 10^5$ Ω·cm or less, more preferably $1 \times 10^4$ Ω·cm or less, and even more preferably $1 \times 10^3$ Ω·cm or less.

The volume resistivity of the conductive member is a value measured using the following method.

In accordance with JIS K6911:1995, a voltage adjusted such that the electric field (applied voltage/sample thickness) is 1000 V/cm is applied to a sheet of the conductive member for 30 seconds using a measuring jig (R12702A/B resistivity chamber, manufactured by Advantest Corporation) and a high resistance meter (R8340A digital ultra-high resistance/micro current meter, manufactured by Advantest Corporation). The current value is then read and calculated using the following formula.

$$\text{Volume resistivity } (\Omega \cdot \text{cm}) = 19.63 \text{ cm}^2 \times \text{applied voltage (V)}/(\text{current value (A)} \times \text{sample thickness (cm)})$$

In view of dynamic conformance, the rubber hardness of the conductive member is preferably 20° or more and 80° or less, more preferably 30° or more and 60° or less, and even more preferably 35° or more and 55° or less.

As used herein, "rubber hardness" refers to Shore A hardness. Shore A hardness conforms to JIS K6253-3:2012. The numerical value of Shore A hardness measured using a type A durometer for a measuring time of 15 seconds is read.

In view of adhesion to the surface of a living body, the surface roughness of a biocontact surface of the conductive member is preferably 5 µm or more and 50 µm or less, more preferably 10 µm or more and 40 µm or less.

As used herein, "surface roughness" refers to the ten-point average roughness Rz prescribed by JIS B0601:1994. The ten-point average roughness Rz is measured using a surface roughness meter (Surfcom 1400A, manufactured by Tokyo Seimitsu, Co., Ltd.) under the following conditions: cut-off: 0.8 mm, measurement length: 4.0 mm, traverse speed: 0.3 mm/sec. The arithmetic average of the ten-point average roughness Rz of three locations is calculated to determine the surface roughness of the biocontact surface.

Bioelectrode

A bioelectrode according to the present exemplary embodiment includes the conductive member according to the present exemplary embodiment as a biocontact portion configured to be in contact with a living body. In the bioelectrode according to the present exemplary embodiment, at least the biocontact portion configured to be in contact with a living body is formed of the conductive member according to the present exemplary embodiment or the entire electrode may be constituted by the conductive member according to the present exemplary embodiment.

The bioelectrode according to the present exemplary embodiment is applied to, for example, an electrode in a biometer for measuring biosignals such as brainwaves, heart rate, and pulse rate. Specifically, the bioelectrode according to the present exemplary embodiment is applied to, for example, 1) a bioelectrode for measuring brainwaves that is to be inserted into the ear canal, 2) bioelectrode for measuring brainwaves that is to be hooked onto the pinna, 3) a bioelectrode for measuring brainwaves that is to be placed on the forehead or over the entire head, and 4) a bioelectrode for measuring pulse rate or heart rate that is to be placed on an arm, a leg, the chest, or the abdomen.

Figure 1:
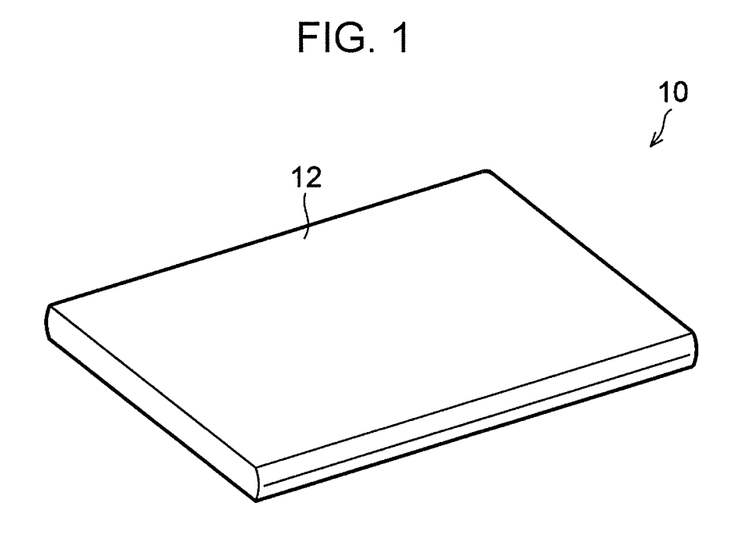
FIG. 1 is a schematic perspective view illustrating an example of a bioelectrode according to the present exemplary embodiment.

The bioelectrode according to the present exemplary embodiment is, for example, in a sheet form. A sheet of the bioelectrode, for example, has a structure constituted only by the conductive member according to the present exemplary embodiment (i.e., a structure entirety constituted by the conductive member according to the present exemplary embodiment, FIG. 1) or a structure including a base and the conductive member according to the present exemplary embodiment disposed on the base (i.e., a structure including the conductive member according to the present exemplary embodiment and other members). In FIG. 1, "10" denotes the bioelectrode and "12" denotes the conductive member.

Figure 2:
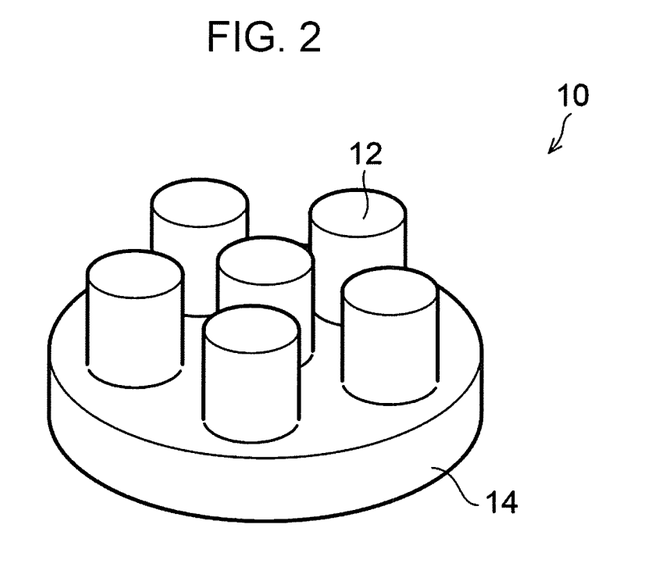
FIG. 2 is a schematic perspective view illustrating another example of a bioelectrode according to the present exemplary embodiment.

The form of the bioelectrode according to the present exemplary embodiment is not limited to a sheet. The form of the bioelectrode according to the present exemplary embodiment is selected according to the intended use. The form of the bioelectrode according to the present exemplary embodiment may be a structure constituted by a base and two or more protruding conductive members disposed on the base (FIG. 2). In FIG. 2, "10" denotes the bioelectrode, "12" denotes the conductive member, and "14" denotes the base.

Biosignal Measuring Device A biosignal measuring device according to the present exemplary embodiment is a device that measures biosignals and includes the bioelectrode according to the present exemplary embodiment.

The biosignal measuring device according to the present exemplary embodiment is suitable for use as a brainwave measuring device that measures brainwaves because of excelling in measurement precision due to low resistance in the bioelectrode.

The biosignal measuring device according to the present exemplary embodiment may be, for example, 1) a brainwave measuring device including the bioelectrode that is to be inserted into the ear canal, 2) a brainwave measuring device including the bioelectrode that is to be hooked onto the pinna, 3) a brainwave measuring device including the bioelectrode that is to be placed on the forehead or over the entire head, and 4) a pulse rate measuring device or heart rate measuring device including the bioelectrode that is to be placed on an arm, a leg, the chest, or the abdomen. The biosignal measuring device according to the present exemplary embodiment has, for example, a configuration illustrated in FIG. 3. A biosignal measuring device 101 includes a bioelectrode 10, a holding member 20 that holds the bioelectrode 10, a biosignal processing unit 22 for processing biosignals (e.g., signals such as brainwaves, pulse rate, and heart rate) obtained by the bioelectrode 10, a display unit 24 that displays various types of information including information on biosignals, an input unit 26 for inputting, for example, operation information into the biosignal measuring device 101, a communication interface 28 that transmits processed signals to external devices, and a control section 30 that controls each of the units of the biosignal measuring device 101.

Figure 3:
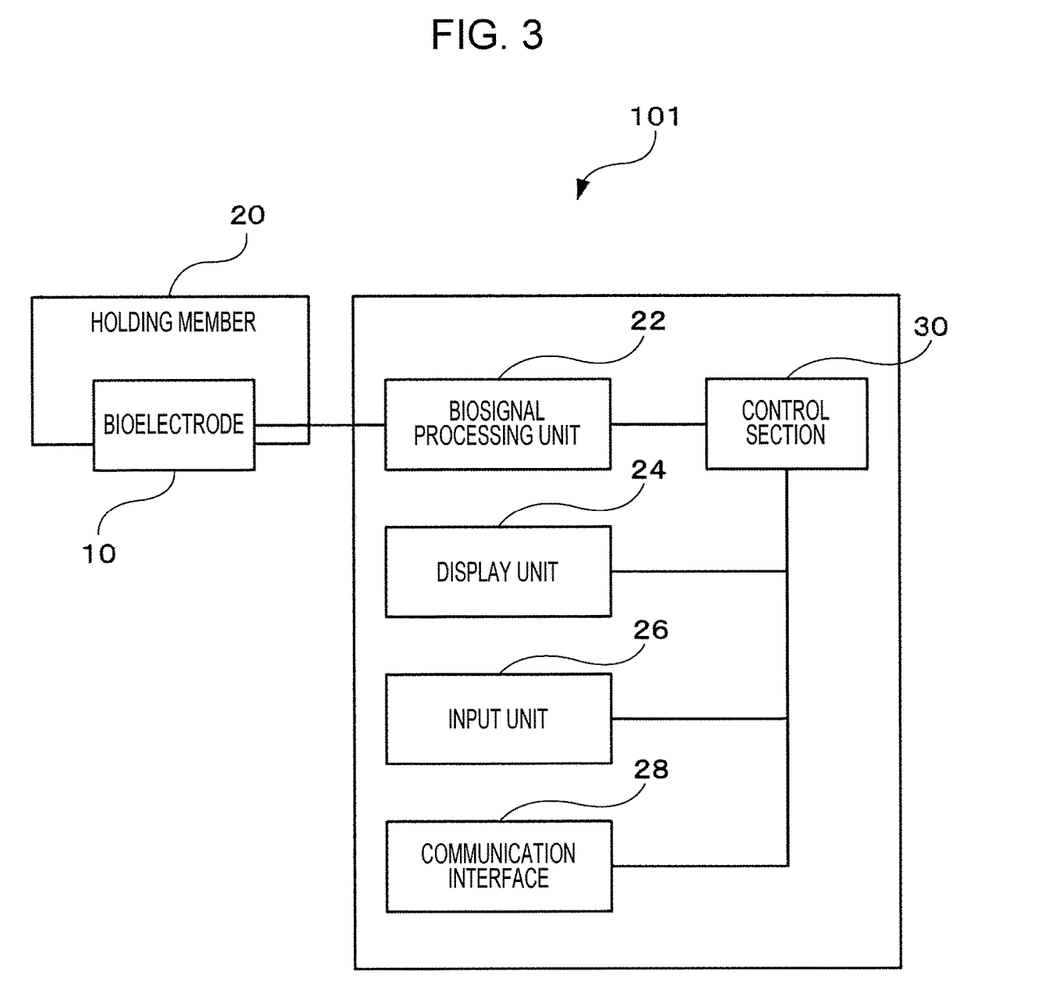
FIG. 3 is a block diagram illustrating an example of a biosignal measuring device according to the present exemplary embodiment.

The holding member 20 is a member having a form depending on the intended use such as being inserted into the ear canal for measuring brainwaves, being hooked onto the pinna for measuring brainwaves, being placed on the forehead or over the entire head for measuring brainwaves, or being placed on an arm, a leg, the chest, or the abdomen for measuring pulse rate or heart rate.

The biosignal processing unit 22 is constituted, for example, by various processing circuits such as a signal amplification circuit.

The display unit 24 is, for example, constituted by a liquid crystal display. The display unit 24 may be in a touch screen format to function as the input unit 26.

The input unit 26 is constituted by various input devices such as a pointing device (e.g., a mouse), a keyboard, and a button.

The communication interface 28 is an interface for communicating with an external device (such as a personal computer for measuring biosignals or a mobile terminal) and employs a standard such as Ethernet (registered trademark), FDDI, or Wi-Fi (registered trademark).

The control section 30 (not illustrated) includes a central processing unit (CPU), a read-only memory (ROM), a random access memory (RAM), a storage, and an input-output interface (I/O). These components are communicably connected to each other via a bus.

The CPU, which is a central processing unit, executes various programs and controls individual units. In other words, the CPU reads a program from the ROM or the storage and executes the program using the RAM as a workspace. The CPU controls the above components and executes various types of arithmetic processing in accordance with the program stored in the ROM or the storage. The ROM stores various programs and various data. The RAM, which serves as a workspace, temporarily stores programs or data. The storage is constituted by a hard disk drive (HDD), a solid state drive (SSD), or a flash memory and stores various programs including an operating system and various data.

The configuration of the biosignal measuring device according to the present exemplary embodiment is not particularly limited, and a configuration suitable for a biosignal to be measured may be used. The biosignal measuring device may be a terminal device that does not display any information on measured biosignals and that transmits the measured biosignals only to external devices.

EXAMPLES

Hereafter, the exemplary embodiment of the disclosure will be described in detail with reference to examples, but the examples are not intended to limit the exemplary embodiment of the disclosure.

Example 1

The following materials are mixed using a pressure kneader to prepare a base compound.
- 100 parts by mass of a silicone rubber raw material (a rubber-like organopolysiloxane that is constituted by 99.825 mol % of a dimethylsiloxane unit, 0.15 mol % of a methylvinylsiloxane unit, and 0.025 mol % of a dimethylvinylsiloxane unit and that has an average degree of polymerization of about 5000)
- 40 parts by mass of a carbon black having a DBP absorption of 130 $cm^3/100$ g (#3030B, manufactured by Mitsubishi Chemical Corporation)
- 20 parts by mass of a carbon black having a DBP absorption of 365 $cm^3/100$ g (EC300J, manufactured by Lion Specialty Chemicals Co., Ltd.)
- 2 parts by mass of fumed silica (AEROSIL R202, manufactured by Evonik Industries AG)
- 0.5 parts by mass of a silane coupling agent (KBM-1003, manufactured by Shin-Etsu Chemical Co., Ltd.)

To the base compound, 1.5 parts by mass of a C-8A curing agent (manufactured by Shin-Etsu Chemical Co., Ltd.) is added to obtain a rubber compound. The rubber compound is put into a mold with a thickness of 2 mm and is heated at 165° C. for 15 minutes (vulcanizing process). The rubber compound is then heated at 200° C. for 8 hours (heating process to remove D3 to D24 cyclic dimethylpolysiloxane) to obtain a rubber sheet. The rubber sheet is cut into a 50 mm square sheet for use as a bioelectrode.

Examples 2 to 14 and Comparative Examples 1 and 2

A rubber sheet is obtained for use as a bioelectrode in the same manner as in Example 1 except that, as indicated in Table 1, the temperature and the time duration in the heating process to remove D3 to D24 cyclic dimethylpolysiloxane ("additional heating temperature" and "additional heating time" mentioned in Table 1) are changed or that the type and the amount (parts by mass) of carbon black are changed.

Performance Evaluation

Measurement of Physical Property Values

The content (ppm) of D3 to D24 cyclic dimethylpolysiloxane, the volume resistivity (Ω·cm), and the rubber hardness (Shore A hardness, °) of the rubber sheets in Examples and Comparative Examples are measured using the above-described measurement methods.

Measurement of Voltage Waveform

An experiment simulating a brainwave measurement is conducted as follows.

A function generator (33120A, manufactured by Hewlett Packard Company, 15 MHz function/arbitrary waveform generator) and a frequency measuring device are provided.

First, to obtain a reference voltage waveform, the output side of the function generator and the input side of the frequency measuring device are connected to each other without a bioelectrode interposed therebetween. This connection is performed using two 10-cm-long alligator clip cables jointed together. An AC voltage signal of 10 μV/10 Hz is transmitted from the function generator, the voltage waveform is measured using the frequency measuring device, and the voltage waveform data is output to a personal computer (PC). The average value of peak-to-peak values of 50 cycles (This average value is referred to as "Rpp") is then determined.

Next, a bioelectrode (rubber sheet) is inserted between the two alligator clip cables, and the function generator and the frequency measuring device are connected to each other with the bioelectrode interposed therebetween (i.e., the connection order is as follows: function generator-alligator clip cable-bioelectrode-alligator clip cable-frequency measuring device). An AC voltage signal of 10 μV/10 Hz is transmitted from the function generator, the voltage waveform is measured using the frequency measuring device, and the voltage waveform data is output to a personal computer (PC). The average value of peak-to-peak values of 50 cycles (This average value is referred to as "Spp") is then determined.

The difference percentage is determined by the following formula, and the results are classified as A to D.

Formula: $|Rpp-Spp|/Rpp \times 100(\%)$

A (very good): The difference percentage is 0.5% or less.
B (good): The difference percentage is more than 0.5% and 1.0% or less.
C (fair): The difference percentage is more than 1.0% and 1.5% or less.
D (poor): The difference percentage is more than 1.5%.

The numbers enclosed in parentheses in Table 1 are values of (Rpp−Spp).

TABLE 1

| DBP absorption-based category | | Product name | DBP absorption ($cm^3/100$ g) | Example 1 | Example 2 | Example 3 | Example 4 | Comparative Example 1 |
|---|---|---|---|---|---|---|---|---|
| Silicone rubber | | | | 100 | 100 | 100 | 100 | 100 |
| Carbon black | First | Asahi Thermal | 28 | | | | | |
| | | Asahi #50U | 63 | | | | | |
| | | #3030B | 130 | 40 | 40 | 40 | 40 | 40 |
| | Second | FX35 | 220 | | | | | |
| | | ECP200L | 300 | | | | | |
| | | EC300J | 365 | 20 | 20 | 20 | 20 | 20 |
| | | LIONITE CB | 378 | | | | | |
| | | HS 500 | 500 | | | | | |

TABLE 1-continued

| | | | | | | | |
|---|---|---|---|---|---|---|---|
| Fumed silica | | | | 2 | 2 | 2 | 2 | 2 |
| Silane coupling agent | | | | 0.5 | 0.5 | 0.5 | 0.5 | 0.5 |
| C-8A curing agent | | | | 1.5 | 1.5 | 1.5 | 1.5 | 1.5 |
| Difference in DBP absorption | | | | 235 | 235 | 235 | 235 | 235 |
| Weighted average of DBP absorption | | | | 208 | 208 | 208 | 208 | 208 |
| Additional heating temperature (° C.) | | | | 200 | 100 | 300 | 80 | None |
| Additional heating time (hr) | | | | 8 | 14 | 3 | 8 | None |
| Total content of D3 to D24 cyclic DMPS (ppm) | | | | 1705 | 2651 | 1527 | 4523 | 8692 |
| Total content of D3 to D12 cyclic DMPS (ppm) | | | | 202 | 322 | 123 | 463 | 711 |
| Common logarithm of volume resistivity (log Ω · cm) | | | | 1.0 | 1.1 | 0.8 | 4.5 | 8.5 |
| Rubber hardness (Shore A hardness, °) | | | | 56 | 48 | 58 | 46 | 45 |
| Voltage waveform | | | | A (0.2) | A (0.2) | A (0.1) | B (0.45) | D (−40.3) |

| | DBP absorption-based category | Product name | DBP absorption (cm³/100 g) | Comparative Example 2 | Example 5 | Example 6 |
|---|---|---|---|---|---|---|
| Silicone rubber | | | | 100 | 100 | 100 |
| Carbon black | First | Asahi Thermal | 28 | | | |
| | | Asahi #50U | 63 | | | |
| | | #3030B | 130 | 40 | 60 | 50 |
| | Second | FX35 | 220 | | 15 | 20 |
| | | ECP200L | 300 | | | |
| | | EC300J | 365 | 20 | | |
| | | LIONITE CB | 378 | | | |
| | | HS 500 | 500 | | | |
| Fumed silica | | | | 2 | 2 | 2 |
| Silane coupling agent | | | | 0.5 | 0.5 | 0.5 |
| C-8A curing agent | | | | 1.5 | 1.5 | 1.5 |
| Difference in DBP absorption | | | | 235 | 90 | 90 |
| Weighted average of DBP absorption | | | | 208 | 148 | 156 |
| Additional heating temperature (° C.) | | | | 60 | 200 | 200 |
| Additional heating time (hr) | | | | 8 | 8 | 8 |
| Total content of D3 to D24 cyclic DMPS (ppm) | | | | 5511 | 1753 | 1772 |
| Total content of D3 to D12 cyclic DMPS (ppm) | | | | 683 | 221 | 205 |
| Common logarithm of volume resistivity (log Ω · cm) | | | | 5.6 | 0.8 | 1.1 |
| Rubber hardness (Shore A hardness, °) | | | | 45 | 47 | 50 |
| Voltage waveform | | | | D (1.8) | A (0.2) | A (0.3) |

| | DBP absorption-based category | Product name | DBP absorption (cm³/100 g) | Example 7 | Example 8 | Example 9 | Example 10 | Example 11 |
|---|---|---|---|---|---|---|---|---|
| Silicone rubber | | | | 100 | 100 | 100 | 100 | 100 |
| Carbon black | First | Asahi Thermal | 28 | | | | | 40 |
| | | Asahi #50U | 63 | | | 40 | 10 | |
| | | #3030B | 130 | 60 | 50 | | | |
| | Second | FX35 | 220 | | | | | |
| | | ECP200L | 300 | 10 | | | | |
| | | EC300J | 365 | | | | | 30 |
| | | LIONITE CB | 378 | | | 25 | 30 | |
| | | HS 500 | 500 | | 15 | | | |
| Fumed silica | | | | 2 | 2 | 2 | 2 | 2 |
| Silane coupling agent | | | | 0.5 | 0.5 | 0.5 | 0.5 | 0.5 |
| C-8A curing agent | | | | 1.5 | 1.5 | 1.5 | 1.5 | 1.5 |
| Difference in DBP absorption | | | | 170 | 370 | 315 | 315 | 337 |
| Weighted average of DBP absorption | | | | 154 | 215 | 184 | 299 | 172 |
| Additional heating temperature (° C.) | | | | 200 | 200 | 200 | 200 | 200 |
| Additional heating time (hr) | | | | 8 | 8 | 8 | 8 | 8 |
| Total content of D3 to D24 cyclic DMPS (ppm) | | | | 1723 | 1786 | 1756 | 1756 | 1725 |
| Total content of D3 to D12 cyclic DMPS (ppm) | | | | 211 | 225 | 231 | 207 | 207 |
| Common logarithm of volume resistivity (log Ω · cm) | | | | 1.0 | 0.9 | 0.8 | 1.7 | 1.3 |
| Rubber hardness (Shore A hardness, °) | | | | 45 | 45 | 54 | 57 | 55 |
| Voltage waveform | | | | A (0.3) | A (0.3) | A (0.4) | B (0.8) | A (0.2) |

| | DBP absorption-based category | Product name | DBP absorption (cm³/100 g) | Example 12 | Example 13 | Example 14 |
|---|---|---|---|---|---|---|
| Silicone rubber | | | | 100 | 100 | 100 |
| Carbon black | First | Asahi Thermal | 28 | 30 | | |
| | | Asahi #50U | 63 | | | |
| | | #3030B | 130 | 50 | | |

TABLE 1-continued

| | | | | | | |
|---|---|---|---|---|---|---|
| Second | FX35 | 220 | | 10 | | |
| | ECP200L | 300 | | | | |
| | EC300J | 365 | | | 40 | |
| | LIONITE CB | 378 | | | | |
| | HS 500 | 500 | | 30 | | |
| Fumed silica | | | 2 | 2 | 2 | |
| Silane coupling agent | | | 0.5 | 0.5 | 0.5 | |
| C-8A curing agent | | | 1.5 | 1.5 | 1.5 | |
| Difference in DBP absorption | | | 102 | 280 | — | |
| Weighted average of DBP absorption | | | 92 | 430 | 365 | |
| Additional heating temperature (° C.) | | | 200 | 200 | 200 | |
| Additional heating time (hr) | | | 8 | 8 | 8 | |
| Total content of D3 to D24 cyclic DMPS (ppm) | | | 1762 | 1798 | 1752 | |
| Total content of D3 to D12 cyclic DMPS (ppm) | | | 212 | 203 | 225 | |
| Common logarithm of volume resistivity (log Ω · cm) | | | 4.5 | 0.7 | 0.7 | |
| Rubber hardness (Shore A hardness, °) | | | 44 | 76 | 70 | |
| Voltage waveform | | | C (1.3) | A (0.3) | A (0.2) | |

The above results reveal that the bioelectrode according to the present exemplary embodiment excels in precision in the measurement of voltage waveforms compared with the bioelectrodes in Comparative Examples.

The details of the carbon blacks described in Table 1 are as follows.

Asahi Thermal: carbon black, manufactured by Asahi Carbon Co., Ltd., DBP absorption: 28 cm$^3$/100 g, average primary particle size: 80 nm.

Asahi #50U: carbon black, manufactured by Asahi Carbon Co., Ltd., DBP absorption: 63 cm$^3$/100 g, average primary particle size: 70 nm.

3030B: carbon black, manufactured by Mitsubishi Chemical Corporation, DBP absorption: 130 cm$^3$/100 g, average primary particle size: 55 nm.

FX35: carbon black, manufactured by Denka Co., Ltd., DBP absorption: 220 cm$^3$/100 g, average primary particle size: 26 nm.

ECP200L: Ketjen black, manufactured by Lion Specialty Chemicals Co., Ltd., DBP absorption: 300 cm$^3$/100 g, average primary particle size: 35 nm.

EC300J: Ketjen black, manufactured by Lion Specialty Chemicals Co., Ltd., DBP absorption: 365 cm$^3$/100 g, average primary particle size: 39.5 nm.

LIONITE CB: carbon black, manufactured by Lion Specialty Chemicals Co., Ltd., DBP absorption: 378 cm$^3$/100 g, average primary particle size: 28 nm.

HS 500: carbon black, manufactured by Asahi Carbon Co., Ltd., DBP absorption: 500 cm$^3$/100 g, average primary particle size: 38 nm.

The foregoing description of the exemplary embodiment of the present disclosure has been provided for the purposes of illustration and description. It is not intended to be exhaustive or to limit the disclosure to the precise forms disclosed. Obviously, many modifications and variations will be apparent to practitioners skilled in the art. The embodiment was chosen and described in order to best explain the principles of the disclosure and its practical applications, thereby enabling others skilled in the art to understand the disclosure for various embodiments and with the various modifications as are suited to the particular use contemplated. It is intended that the scope of the disclosure be defined by the following claims and their equivalents.

What is claimed is:

1. A conductive member comprising:
   silicone rubber;
   a conductive agent; and
   cyclic dimethylpolysiloxane having 3 to 24 silicon atoms,
   wherein a total content of cyclic dimethylpolysiloxane having 3 to 24 silicon atoms is 5000 ppm or less,
   the conductive agent contains a carbon black, the carbon black contains a first carbon black having a DBP absorption of less than 200 cm3/100 g and a second carbon black having a DBP absorption of not less than 200 cm3/100 g,
   a total content of the carbon black is 50 parts by mass or more and 70 parts by mass or less with respect to 100 parts by mass of the silicone rubber, and a total content of the second carbon black is 15 parts by mass or more and 25 parts by mass or less with respect to 100 parts by mass of the silicone rubber, and a total content of the first carbon black is 25 parts by mass or more and 55 parts by mass or less with respect to 100 parts by mass of the silicone rubber.

2. The conductive member according to claim 1, wherein the total content of cyclic dimethylpolysiloxane having 3 to 24 silicon atoms is 3000 ppm or less.

3. The conductive member according to claim 1, wherein a total content of cyclic dimethylpolysiloxane having 3 to 12 silicon atoms is 500 ppm or less.

4. The conductive member according to claim 3, wherein the total content of cyclic dimethylpolysiloxane having 3 to 12 silicon atoms is 300 ppm or less.

5. The conductive member according to claim 1, wherein an absolute value of a difference between the DBP absorption of the first carbon black and the DBP absorption of the second carbon black is not less than 70 cm$^3$/100 g and not more than 400 cm$^3$/100 g.

6. The conductive member according to claim 1, wherein the conductive member has a volume resistivity of $1 \times 10^5$ Ω·cm or less.

7. The conductive member according to claim 1, wherein the conductive member has a rubber hardness of 30° or more and 60° or less.

8. A bioelectrode comprising:
   the conductive member according to claim 1 serving as a biocontact portion configured to be in contact with a living body.

9. A biosignal measuring device comprising:
   the bioelectrode according to claim 8,
   wherein the biosignal measuring device measures a biosignal.

10. The biosignal measuring device according to claim 9, wherein the biosignal is a brainwave.

11. The conductive member according to claim 1, wherein the total content of cyclic dimethylpolysiloxane having 3 to 24 silicon atoms is 500 ppm or more.

12. The conductive member according to claim 1, wherein a total content of cyclic dimethylpolysiloxane having 3 to 12 silicon atoms is 100 ppm or more.

* * * * *